(12) United States Patent
Nadeau

(10) Patent No.: US 9,433,524 B2
(45) Date of Patent: Sep. 6, 2016

(54) PORTABLE NEONATAL INTENSIVE CARE UNIT

(71) Applicant: Marc R Nadeau, St. Petersburg, FL (US)

(72) Inventor: Marc R Nadeau, St. Petersburg, FL (US)

(*) Notice: Subject to any disclaimer, the term of this patent is extended or adjusted under 35 U.S.C. 154(b) by 161 days.

(21) Appl. No.: 14/446,749

(22) Filed: Jul. 30, 2014

(65) Prior Publication Data

US 2015/0196423 A1 Jul. 16, 2015

Related U.S. Application Data

(60) Provisional application No. 61/927,541, filed on Jan. 15, 2014.

(51) Int. Cl.
*A61G 11/00* (2006.01)
*A61F 7/00* (2006.01)

(52) U.S. Cl.
CPC .......... *A61F 7/0053* (2013.01); *A61G 11/006* (2013.01); *A61G 11/009* (2013.01); *A61F 2007/0054* (2013.01); *A61G 2200/14* (2013.01); *A61G 2203/46* (2013.01); *A61G 2210/30* (2013.01); *A61G 2210/90* (2013.01)

(58) Field of Classification Search
CPC .......... A61F 7/08; A61F 7/0053–7/12; A61F 2007/0054; A61G 10/00–10/02; A61G 11/00–11/009; A61G 2200/14; A61G 2203/46; A61G 2210/30; A61G 2210/70; A61G 2210/90; A47C 27/085; A47C 21/048; A47C 21/04; A47D 11/007; A47D 9/00; A47D 9/004; A47D 7/00
See application file for complete search history.

(56) References Cited

U.S. PATENT DOCUMENTS

| | | | |
|---|---|---|---|
| 2,708,927 A * | 5/1955 | Dixon | A61G 11/00 160/180 |
| 3,470,866 A * | 10/1969 | Gittelson | A61G 11/00 600/22 |
| 4,038,973 A * | 8/1977 | Moore | A61B 5/1107 177/144 |
| 4,079,728 A * | 3/1978 | Gatts | A47D 9/02 5/422 |
| 4,168,554 A * | 9/1979 | Hindes | A61H 31/008 5/625 |
| 4,321,913 A | 3/1982 | Maluta et al. | |
| 4,936,824 A * | 6/1990 | Koch | A61G 11/00 128/205.26 |
| 4,974,272 A * | 12/1990 | Liu | A47C 21/044 5/422 |
| 6,094,758 A * | 8/2000 | Renfro | A47C 27/085 114/343 |
| 6,216,291 B1 * | 4/2001 | Eads | A61G 7/0526 135/121 |
| 6,386,231 B1 * | 5/2002 | Elser | F04B 49/03 137/565.12 |
| 6,428,465 B1 | 8/2002 | Belsinger, Jr. | |
| 6,709,384 B1 | 3/2004 | Donnelly et al. | |
| 7,886,548 B1 | 2/2011 | Graves | |
| 2001/0016677 A1 | 8/2001 | Poole et al. | |
| 2006/0218727 A1 * | 10/2006 | Jones | A61G 11/00 5/655 |
| 2010/0168502 A1 | 7/2010 | Delaporte et al. | |
| 2012/0215054 A1 * | 8/2012 | Rodrigues | A61G 11/00 600/22 |
| 2012/0220817 A1 | 8/2012 | Castillon | |
| 2012/0305231 A1 | 12/2012 | Liang et al. | |
| 2013/0204074 A1 | 8/2013 | Belval et al. | |

\* cited by examiner

*Primary Examiner* — John Lacyk
(74) *Attorney, Agent, or Firm* — Thomas Frost

(57) ABSTRACT

The present invention relates to a portable, self-contained, neonatal intensive care unit (NICU) providing heating (or cooling) for the patient by controlled exchange of thermal energy between a transparent enclosure that houses the infant and an internal reservoir. The invention has no requirement for electrical power. The internal reservoir utilizes water that is heated (or cooled) by an external source. The micro-environment inside the transparent enclosure for the infant and the water inside the internal reservoir are thermally and acoustically isolated in order to minimize heat and sound exchange with the ambient environment.

17 Claims, 10 Drawing Sheets

PORTABLE NEONATAL INTENSIVE CARE UNIT

BACKGROUND OF INVENTION

The present invention relates to a portable neonatal care unit having means for obtaining operational temperature by controlled exchange of thermal energy between the transparent infant enclosure and an internal reservoir. Electrical power is not required.

A Neonatal Intensive Care Unit (NICU), which is also referred to as an incubator or an isolette, is used primarily in the hospitals and maternal care centers of industrial nations to maintain a controlled environment for infants, especially premature babies, under optimum conditions until they are strong enough to survive in the ambient, natural environment. These apparatuses are technically complex and are equipped with sophisticated electronic sensors for monitoring the environment and the vitals of the patient. Each NICU requires an electrical power source for operation. The physical unit and the on-board electronics are fabricated for proper servicing and maintenance by knowledgeable professionals in a properly-equipped, healthcare facility.

Modern, commercial NICU's are largely unavailable to physicians, health care workers, midwives, and families, who are located outside of industrial nations and/or in disaster zones. In addition to the high cost of acquisition, the complexity of these units and technical operation makes the devices largely unattainable for users without special training. Significant financial resources are also required to service the devices, provide an inventory of spare components, and retain technical staff to affect the proper maintenance and repairs.

In order to make NICU's more universally available to patients, especially those who are born in remote locales, disaster zones, and/or developing nations, the present invention has been developed as a robustly-built device that is easy to deploy in virtually any location inhabited by humans. Optimal, operational temperature is attained by controlled exchange of thermal energy between the transparent enclosure for the infant and an internal reservoir. Operation is simple for all users, including those who are illiterate. All components in a proximity to the infant are non-toxic. The whole invention may be cleaned with soap and fresh water.

The present invention does not require connection to an electrical power source. A warm environment for the infant is provided through the utilization of virtually any external heat source, including but not limited to, solar radiation, hot water from a geothermal source, wood fire, gas or kerosene-fired water heater, oil burner, coal heater, or electric water heater. Furthermore, the infant enclosure and the internal reservoir of the NICU are engineered to maintain temperature by minimizing thermal exchange with the ambient environment.

By design, the present invention may also be utilized to help reduce the body temperature of an infant or toddler, who is afflicted with an elevated body temperature as a result of disease, injury, or illness. Cool or cold water may be obtained from external sources, including but not limited to, wells, underground springs, melted snow, or melted ice. A therapeutic, microenvironment may be maintained around the patient even in a location that has no air conditioning.

Under impoverished conditions that are not uncommon in developing nations or in disaster zones, theft or looting of machinery for actual or scrap value is often used as a source of revenue. Unlike modern commercial NICU's, the invention contains components of little or no intrinsic value; hence, would not be a likely target of opportunity.

SUMMARY OF THE INVENTION

The general purpose of the present invention, which will be described subsequently in greater detail, is to provide a new and improved portable neonatal intensive care unit.

To attain this, the present invention comprises an intensive care unit which includes a transparent infant enclosure. Access to the patient is provided in by portholes in the enclosure, as well as by opening doors. Portholes are equipped with meshes to help to isolate the infant from insects and/or airborne contaminants, while providing cross-flow ventilation. In cold environments, solid closures may be fitted to some of the portholes to reduce heat loss while allowing for adequate ventilation.

A hollow mattress, filled with fluid, is positioned within the enclosure. Controlled exchange of thermal energy between the enclosure and a reservoir in fluid connection with the mattress provides heating or cooling. No electrical power is required. The reservoir utilizes water that is heated (or cooled) by an external source. The care unit is mountable on a movable platform.

It is an object of the present invention to provide for a portable neonatal care unit requiring no electrical power for heating or cooling water utilized for heat exchange.

It is also an object of the present invention to provide a platform to transport the care unit.

BRIEF DESCRIPTION OF THE DRAWINGS

The invention will be better understood and objects other than those set forth above will become apparent when consideration is given to the following detailed description thereof. Such description makes reference to the annexed drawings wherein.

REFERENCE NUMERALS IN FIGURES

| | | |
|---|---|---|
| 5 NICU unit | 10 Infant enclosure | 12 Top wall |
| 14 Left wall | 16 Left door | 18 Right door |
| 20 Back wall | 22 Right wall | 24 Inner panel |
| 26 Panel spacer | 28 Porthole spacer | 30 Outer panel |
| 32 Porthole closure-mesh | 34 Mesh | 36 Porthole closure-solid |
| 38 Connector to base unit | 40 Hinge | 42 Catch |

-continued

| | | |
|---|---|---|
| 44 Drain | 46 Porthole | |
| 50 Mattress with coverlet | 52 Top layer of coverlet | 54 Insulation layer |
| 56 Bottom layer of coverlet | 58 Mattress | 60 Inlet port |
| 62 Outlet port | 64 Fill-drain-vent port | 66 Mattress thermometer |
| 68 Closure | 70 Coverlet | |
| 80 Base unit | 82 Mattress retainer | 84 Top of base unit |
| 86 Left access panel | 87 Slot | 88 Compartment drain |
| 90 Right access panel | 92 Support structure | 93 Front side |
| 94 Reservoir | 95 Back side | 96 Pump |
| 97 Bottom | 98 Thermal safety valve | 99 Stiffener |
| 100 Heat exchanger | 102 Reservoir thermometer | 104 Reservoir fill |
| 106 Reservoir vent | 108 Reservoir drain | 110 Sight glass |
| 112 Overfill protection | 114 Seal | 116 Latch |
| 118 Pump handle | 120 Panel fastener | 122 Heat exchanger support |
| 124 Overflow drain | 128 Conduit | |
| 130 Platform | 132 Deck | 134 Chock for reservoir |
| 136 Free caster | 138 Locking caster | |
| 150 Infant enclosure-no doors | 152 Movable top of enclosure | 154 Fixed base of enclosure |
| 156 Fastener for fixed base | 158 Lid stay | 160 Seal for movable top |

DETAILED DESCRIPTION OF THE INVENTION

Figure 1:
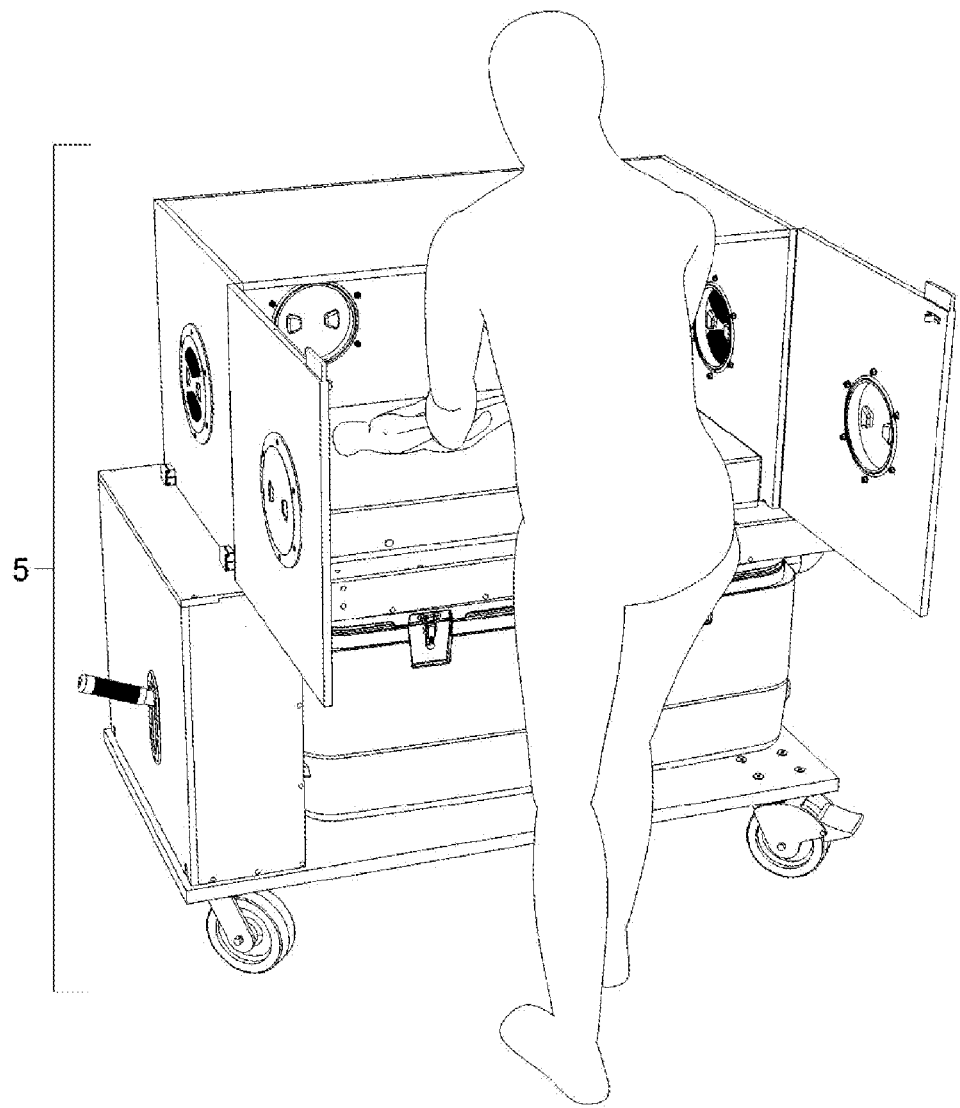
FIG. 1 is a left perspective view of the present invention in an open position.
Figure 2:
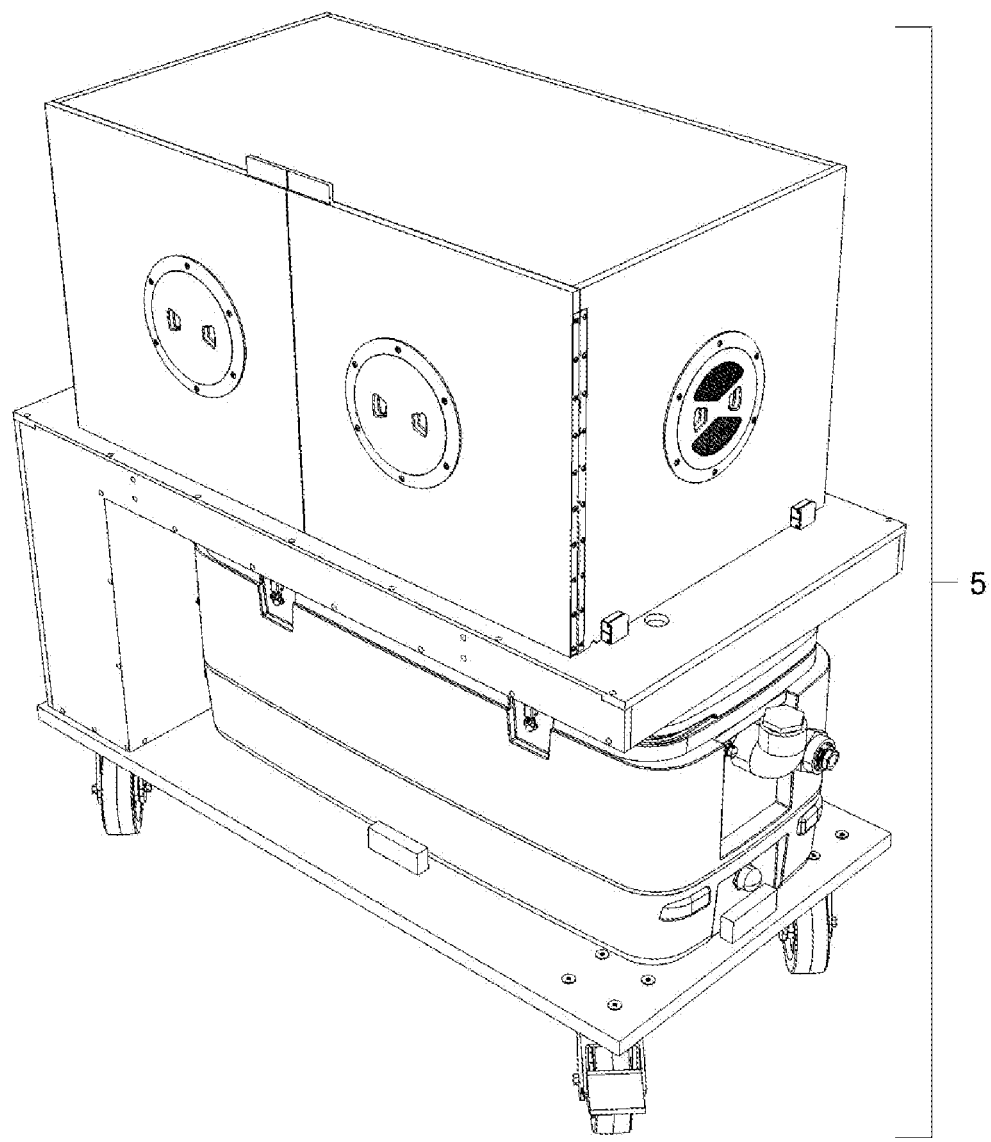
FIG. 2 is a right perspective view of the present invention in a closed position.
Figure 3:
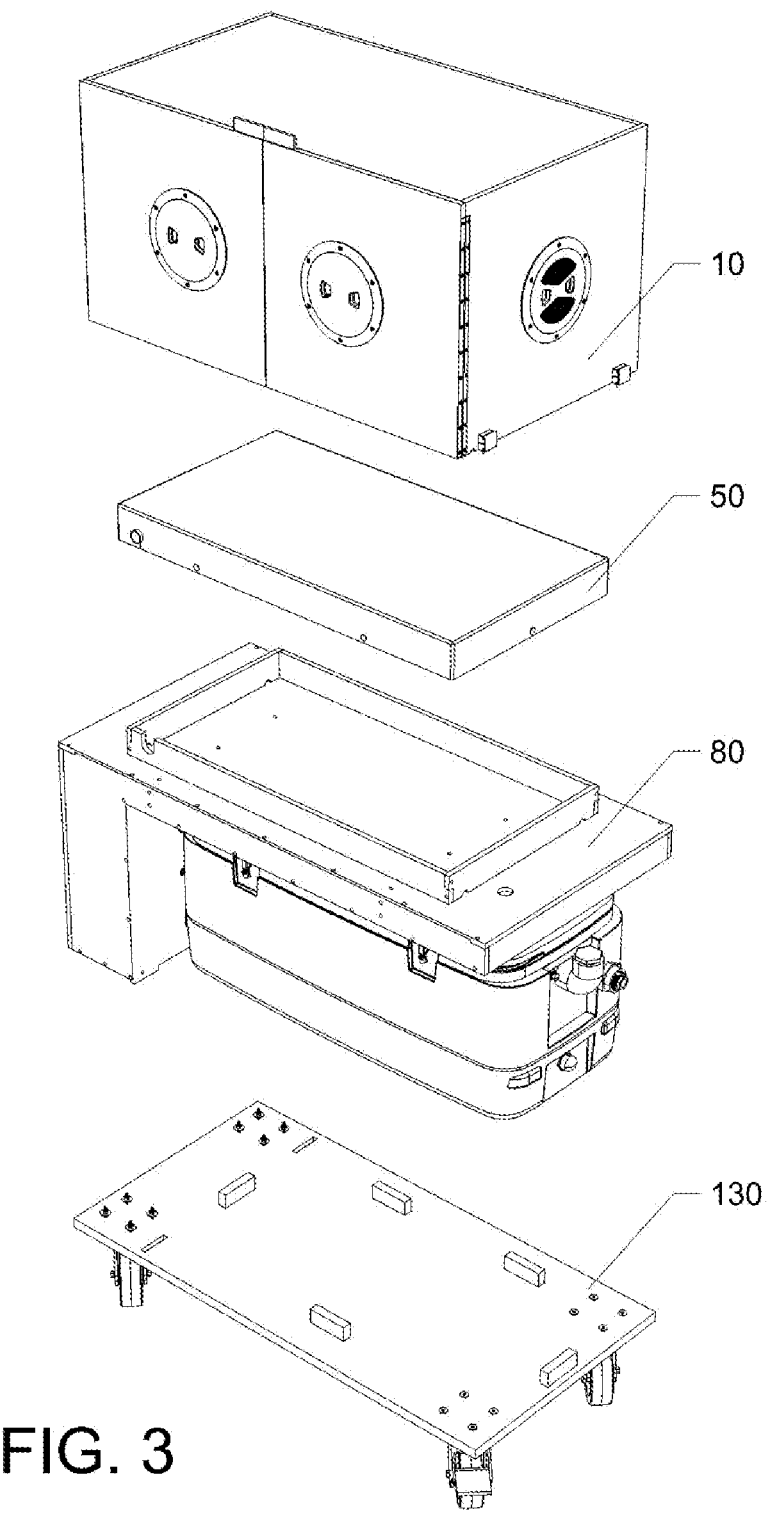
FIG. 3 is an exploded view of the present invention.

In reference to FIGS. 1-8, a neonatal intensive care unit (NICU) 5 is shown. FIG. 3 illustrates an exploded view of the unit 5. A transparent infant enclosure 10 is secured to a base unit 80. A coverlet 70 encasing a mattress 58 upon which to place an infant is positioned inside the enclosure 10. The base unit 80 has a support structure, a liquid reservoir 94, a heat exchanger 100, and a pump 96. The base unit 80 is affixed to a platform 130, which provides a rigid foundation for the incubator and mobility with wheels.

Figure 4:
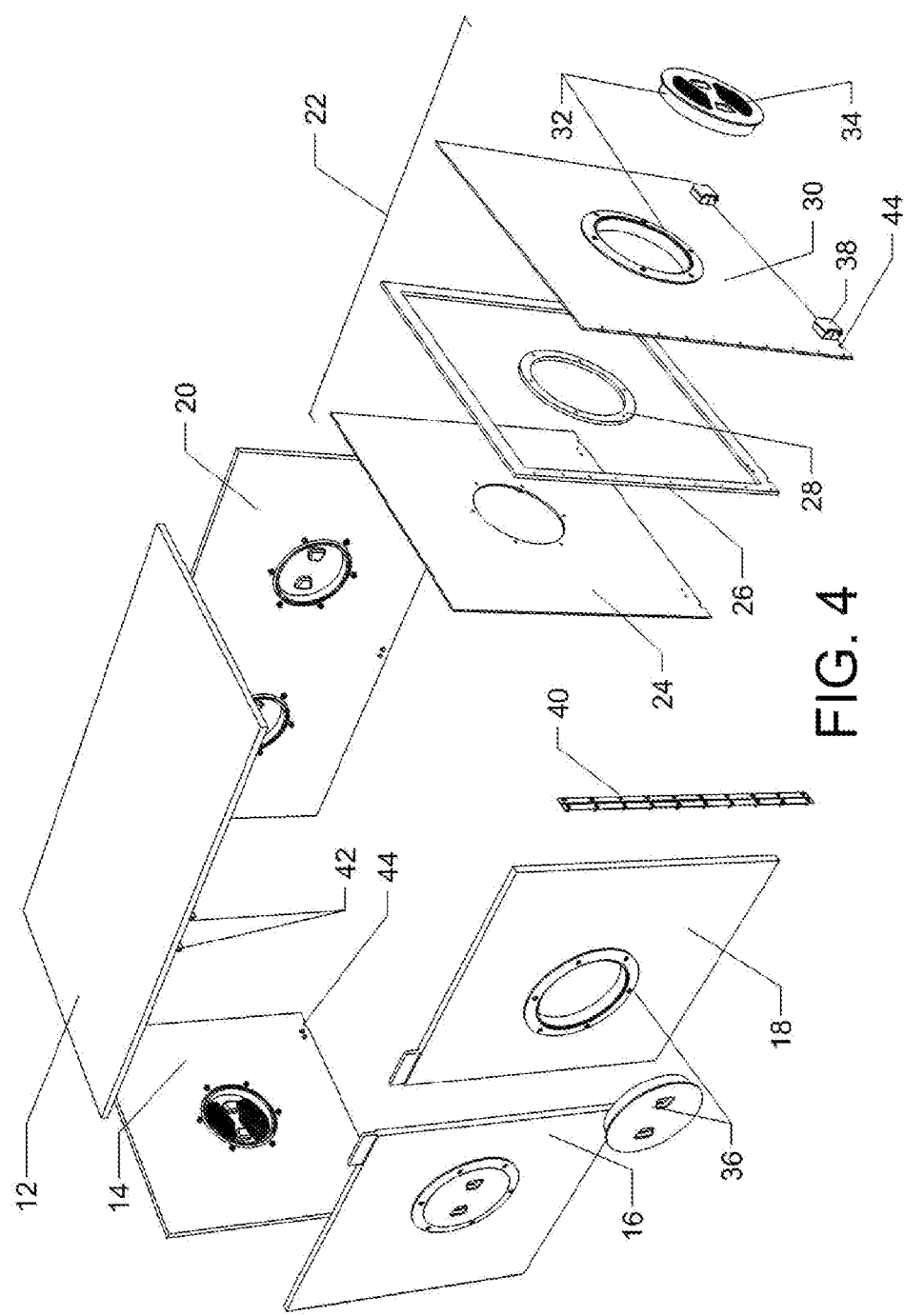
FIG. 4 is an exploded view of an infant enclosure.

The infant enclosure 10 in FIG. 4 has a top wall 12, side walls 14, 22; a back wall 20 and front doors 16, 18; defining a chamber therein. The enclosure 10 may be composed of rigid transparent material, for example, a clear laminated acrylic sheet (polymethyl methacrylate). In some embodiments, the enclosure 10 may be made of Lexan (polycarbonate), PETG (glycol modified polyethylene terphthalate), laminated (safety) glass, or tempered glass. The top wall, side and back walls, and front doors each have laminated construction.

The side walls 14, 22 and the back wall 20 may each be comprised of an integrally formed combination of an inner panel 24 and an outer panel 30 held a uniform distance apart by a panel spacer 26 and a generally circular shaped porthole spacer 28, thereby providing a double wall construction. The panel spacer has a top edge, a bottom edge substantially opposed the top edge, and a pair of parallel side edges between the top edge and the bottom edge. An air gap between the panels provides both a thermal and an acoustic barrier to reduce the rate of heat and sound conduction between the interior of the infant enclosure 10 and the ambient environment. In some embodiments an enclosure 150 may be a one-piece enclosure without doors having the same laminated construction consisting of inner panels 24 and outer panels 30 held a uniform distance apart by panel spacers 26 and porthole spacers 28.

The side walls 14, 22; back wall 20 and doors 16, 18 may be each be formed with one or more portholes 46 defining access passages therethrough. Porthole spacers 28 are positioned juxtaposed the portholes 46 between the inner panels 24 and the outer panels 30. A porthole closure-mesh 32 or a porthole closure-solid 36 may be securely held in place by screws or friction fit. In some embodiments, when the enclosure 150 is a one-piece enclosure without doors, four or more access passages may be formed into the front and sides of the enclosure. The porthole closure-solid 36 that securely locks with the porthole 46 is provided. Alternately, the porthole closure-mesh 32 for ventilation and/or for providing a conduit for life-support tubes/cables for the infant is provided. Each porthole closure-mesh securely interlocks with the porthole 46. The porthole closure-mesh 32 is outfitted with a mesh 34 comprised of metal, plastic, and/or fabric to limit entry of insects and/or small airborne contaminants into the infant enclosure 10, while permitting flow of air. The passages furnish access to the inside the enclosure by physicians, health care workers, and/or the family of the baby without requiring that the enclosure be fully opened. Attendance of the infant through the passages minimizes disturbance to the internal environment of the enclosure.

Each door 16, 18 is pivotally affixed to the adjacent side walls 14, 22 by hinge 40. In some embodiments, the one-piece enclosure 150 without doors is pivotally affixed to the fixed base of the enclosure 154. The hinge means 40 is a piano hinge. Alternatively, butt hinges, glass hinges, or pivot hinges may be utilized.

The doors 16, 18 are secured in a closed position by a catch 42 affixed to a lower surface of the top wall 12. Non-metallic friction catches are illustrated. Alternatively, magnetic catches or spring catches may be used. A simple, non-toxic plastic catch may be preferred for ease of cleaning and for lack of corrosion or degradation to minimize any impact on the infant in the enclosure. In some embodiments with the one-piece enclosure 150 without doors, no catch is required because the weight of the enclosure holds it closed.

Connectors 38 are affixed to a bottom edge of the side walls 14, 22 and back wall 20 to mount on the base unit 80. This hardware permits removal of the infant enclosure 10 from the base unit 80 for transport, major cleaning, or replacement. Quick-release connectors are shown for ease of operation. Connectors 38 are to provide rigidity and maintain the integrity of the infant enclosure 10. A tight fit between the base unit 80 and the infant enclosure 10 is required, in order to maintain the controlled environment inside the enclosure. The alternate embodiment of the one-piece enclosure without doors 150 does not require connectors, since it is attached to the base unit 80 or to a mounting affixed to the base unit 154.

The infant enclosure 10 is outfitted with one or more drains 44. This safety feature provides a means to direct any inadvertent escape of liquids from inside the infant enclosure away from the baby. Multiple drains are preferred to insure proper flow, regardless of the orientation and level of the unit 5.

Figure 5:
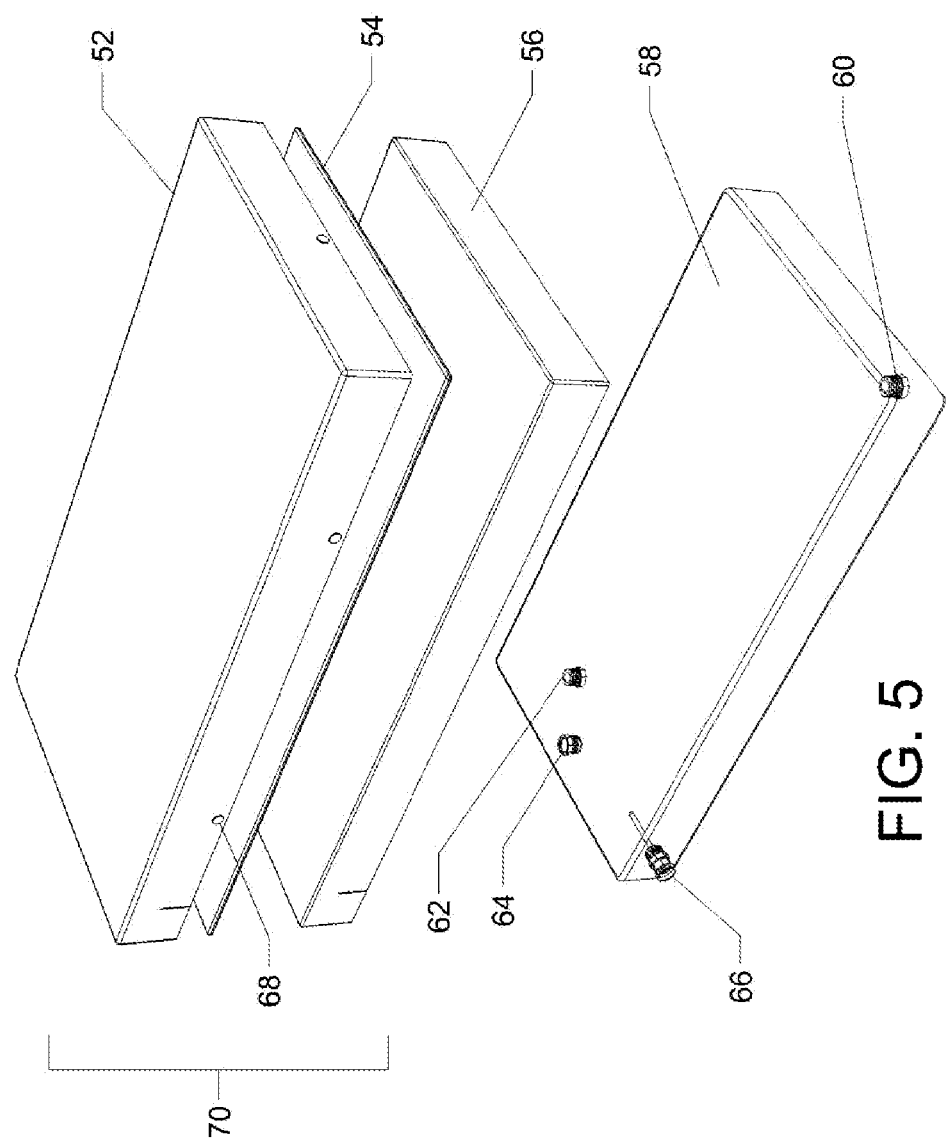
FIG. 5 is an exploded view of a mattress and a coverlet.

FIG. 5 provides an exploded view of the components of the mattress 58 and the coverlet 70. The mattress 58 has an upper, bottom and side surfaces, and is fillable with liquid. The mattress 58 is fabricated from soft, polyvinyl chloride (PVC) plastic, although alternately, other pliable waterproof materials, such as polyethylene or rubberized waterproof fabric, may be used. The mattress 58 is in liquid connection with the base unit 80 by way of conduits 128 and associated connectors. The mattress 58 may be filled with clean, fresh water through a fill-drain-vent port 64, and may be filled to a firm consistency to permit minor oscillation of the water within. After filling, water is pumped through the mattress 58 from the base unit 80 through an inlet port 60. Water returns to the base unit 80 from the mattress 58 through an outlet port 62. The temperature of the water in the mattress 58 may be monitored by a mattress thermometer 66. When not in service, water is drained from the mattress 58 through the fill-drain-vent port 64.

The coverlet 70 lies on top of the mattress 50. The coverlet 50 has a top layer 52, an insulation layer 54, and a bottom layer 56. The top layer 52 is in direct contact with the infant. The top layer 52 may be made from 100% cotton, terry cloth. The fabric is soft, smooth, hypoallergenic, easily laundered, and non-irritating to the skin of the baby. Alternate embodiments for the fabric of the top layer 52 include 100% cotton percale, 100% cotton muslin, or a blended cotton and polyester fabric.

The insulation layer 54 serves to soften the surface of the coverlet 70, to help retain the temperature of the water inside the mattress 58, and to conduct heat between the mattress 58, the baby, and the interior of the infant enclosure 10. The insulation layer may be 100% cotton batting that is integrated into the coverlet 70. Alternate embodiments of the insulation layer 54 include removable material, such as closed-cell polyurethane foam or a non-toxic gel encased in plastic. The insulation layer is removable, and is to be non-absorptive, durable, and easily cleaned and sanitized.

The bottom layer 56 of the coverlet 70 is in direct contact with the top surface of the mattress 58. The bottom layer 56 is made from heavy, cotton duck. The fabric is pliable, stretch-resistant, puncture-resistant, and easily laundered. Alternately, the bottom portion 56 may be made from a synthetic duck, spun polyester fabric, or spun UHMWPE (ultra high molecular weight polyethylene) fabric. The bottom layer 56 of the coverlet 70 reduces the possibility of puncture of the mattress 58 by staff or family caring for the infant. The coverlet 70 may be secured to a mattress retainer 82 with a plurality of closures 68, such as fabric snaps. Alternately, downward-facing fabric hooks attached to the mattress retainer 82 may hold the coverlet 70 in place through button-holes or cords sewn therein. The coverlet 70 may be placed over the mattress 58 after each laundering. It provides a soft barrier between the infant and the mattress 58, while not wholly modifying the flotation properties of the mattress.

Figure 6:
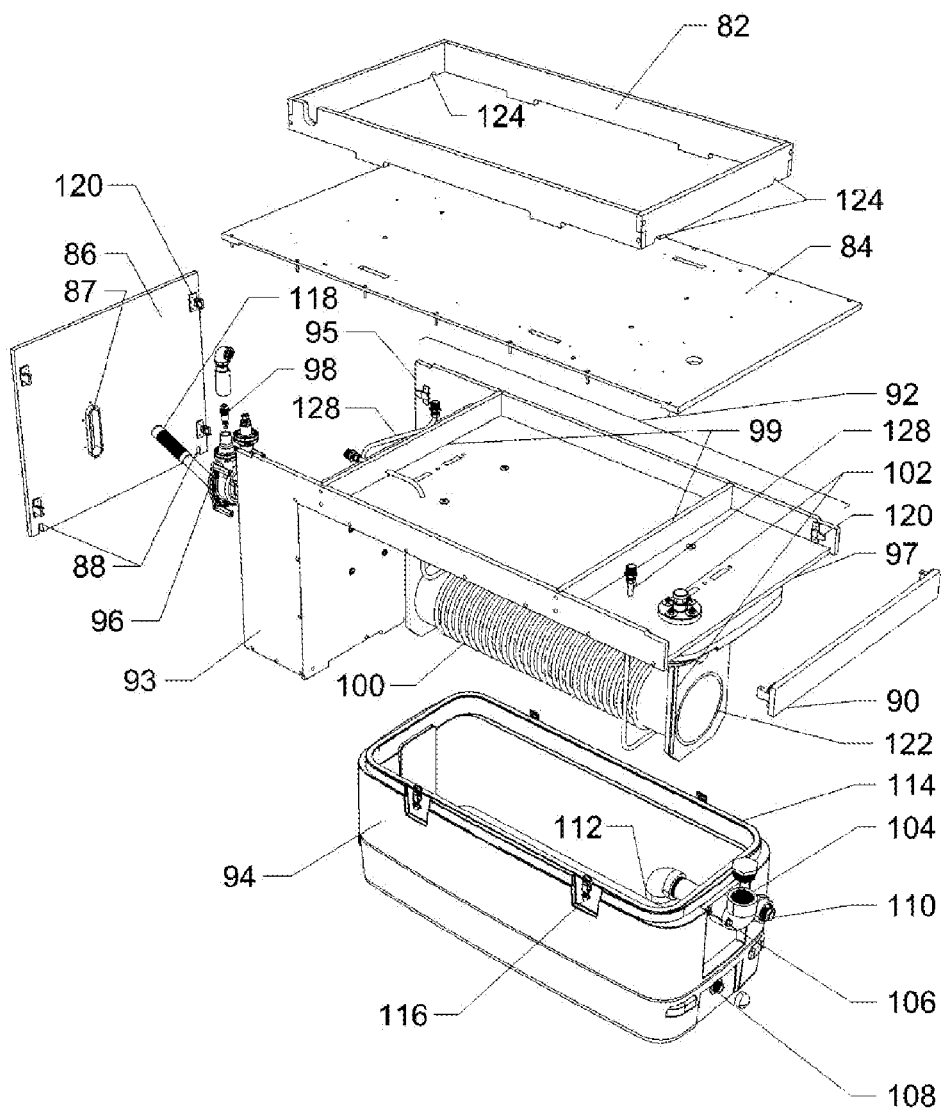
FIG. 6 is an exploded view of a base unit.

The base unit 80 is illustrated in FIG. 6. The unit 80 includes a support structure 92 having a front wall 93, a back wall 95, a top platform 84 and a bottom platform 97 that forms the top of the reservoir 94. Stiffeners 99 help to provide rigidity to the support structure 92. The top panel 84 is affixed to a top edge of the front wall 93, the back wall 95 and stiffeners 99. The support structure 92 may be fabricated from wood, plastic, metal or fiberglass reinforced plastic (FRP). The infant enclosure 10 is mounted on the top platform 84. A mattress retainer 82 is affixed to the top platform 84. The mattress 58 is secured in the mattress retainer 82. The rigid structure of the mattress retainer 82 serves to protect the sides of the mattress 58 and furnish attachment points for the closures 68 that hold the coverlet 70 in place. The mattress retainer 82 is outfitted with one or more overflow drains 124. This safety feature provides a means to direct any inadvertent escape of liquids from the mattress 58 away from the patient. Multiple drains are preferred to insure proper flow, regardless of the orientation and level of the unit 5.

A left access panel 86 and a right access panel 90 are affixed to the support structure 92 with panel fasteners 120. In alternate embodiments, only a single access panel may be required. The panels 86, 90 are detachable for servicing. Accumulated water resulting from damage or servicing of the pump 96 or conduits 128 is dispersed by compartment drains 88.

The pump 96 is affixed to the support structure 92. The pump 96 may be manually actuated with a pump handle 118 that protrudes through a slot 87 defined through the left access panel 86. In some embodiments, additional non-manual pump(s) may be installed. The present invention utilizes a marine diaphragm pump for simplicity, light weight, and durability. Alternate embodiments of the pump 96 may include a piston, rotary vane, or centrifugal pump. Manual operation of the pump 96 is a key to deployment of the unit 5 in the field or in rustic conditions without a portable or a permanent electrical power supply.

A heat exchanger 100 is mounted to the support structure 92 by an exchanger support 122. The heat exchanger 100 consists of coiled copper tubing that is immersed in the water in a reservoir 94. It is connected to the pump 96 and the mattress 58 with conduits 128. Alternate embodiments of the material for the heat exchanger 100 may be stainless steel, galvanized steel, aluminum, bronze, or ceramics. An alternate configuration to the tubular, immersion-type heat exchanger of the present invention may be a plate heat exchanger. A plate heat exchanger may be immersed in the reservoir 94 or have the reservoir 94 situated inside of the heat exchanger 100. A plate heat exchanger may also have a dedicated drain for emptying water therein.

The reservoir 94 is an enclosed container into which hot (or cold) water may be added to provide the medium for thermal transfer to/from the heat exchanger circuit. The reservoir 94 may be outfitted with a fill 104 into which water is poured from a container or hose. A vent 106, located in the top of the reservoir 94, allows the egress of air while filling or the entry of air while draining. Both the fill 104 and the vent 106 are fitted with an overfill protection conduit 112 to prevent filling the reservoir 94 in excess of its capacity. The level of water in the reservoir 94 may be monitored with a sight glass 110. A drain 108 at a base of the reservoir 94 permits removal of water that has cooled or for emptying the reservoir 94 completely for transport or storage. The reservoir may be secured to the support structure 92 with latches 116 and/or adhesive. The reservoir has a lip on its upper edge where it joins the bottom 97 of the support structure 92. The lip may be fitted with a flexible seal 114 to limit the escape of heat/cold or the entry of foreign debris through a gap between the reservoir and the bottom 97 of the support structure 92. The temperature of water inside the reservoir 94 may be monitored by the reservoir thermometer 102.

The reservoir 94 has an outer surface and an inner surface defining a cavity, and an insulating layer between the outer and inner surfaces. The composition of the inner surface of the reservoir 94 in contact with the heated (or cooled) water limits the temperature of water that may be used. In the present invention, the reservoir 94 is constructed from high density polyethylene (HDPE) plastic. The upper temperature limit of water for chronic use is 140° F. (60° C.). Alternate embodiments of the materials for the surface of the reservoir 94 in contact with heated or cooled water may be as follows: sheet metal—stainless steel, aluminum, or galvanized steel; fiberglass reinforced plastic (FRP); ABS plastic; polyurethane plastic; wood. When using sheet metal for the surface of the reservoir that is exposed to heated water, the upper temperature limit of water for chronic use is 212° F. (100° C.). If sheet metal is employed, it is to be isolated from other plastics with a high-temperature silicone elastomer or equal. Using very hot water in the reservoir can provide more efficient heat exchange and increase the duration between re-fillings of the reservoir with hot water.

The insulating layer of the reservoir 94 is formed of rigid foam. The present invention uses polystyrene foam. Alternate embodiments include polyurethane foam, biodegradable foams, starch, a liquid-filled liner, or an air gap. If the exposed surface of the reservoir 94 is sheet metal, insulation made from high-temperature fiberglass batting or a liquid-filled liner adjacent to the metal may be employed in addition to the rigid foam.

The outer surface of the reservoir 94 may be made from high density polyethylene (HDPE), which is impact resistant, scuff resistant, waterproof, and easy to clean with soap and water. Alternate embodiments for the outer surface of the reservoir may be nylon, polyurethane, polypropylene, wood, metal, and fiberglass reinforced plastic (FRP). The construction of the reservoir 94 from plastic and/or sheet metal with rigid foam provides a light weight structure with the necessary durability to use in field or rustic conditions.

The mattress 58, heat exchanger 100, pump 96, and associated conduits 128 may be filled with water through the fill-drain-vent port 64. An alternate embodiment may be the inclusion of a separate drain at the bottom of the heat exchanger 100 or below the mattress 58. These components form a closed circuit through which water is pumped. The heat exchanger 100 is immersed in water in the reservoir 94. The water for the reservoir 94 is heated (or cooled) externally before pouring into the reservoir. When water in the closed circuit flows through the heat exchanger 100, it is heated (or cooled) by thermal transfer with the water in the reservoir 94. The temperature of the mattress 58 and the infant enclosure 10 may be regulated by this controlled thermal transfer. In order to protect the infant from exposure to excessive temperatures, the closed circuit may be outfitted with a thermal safety valve 98 that closes when the water inside the circuit exceeds a safe temperature for the patient.

Figure 7:
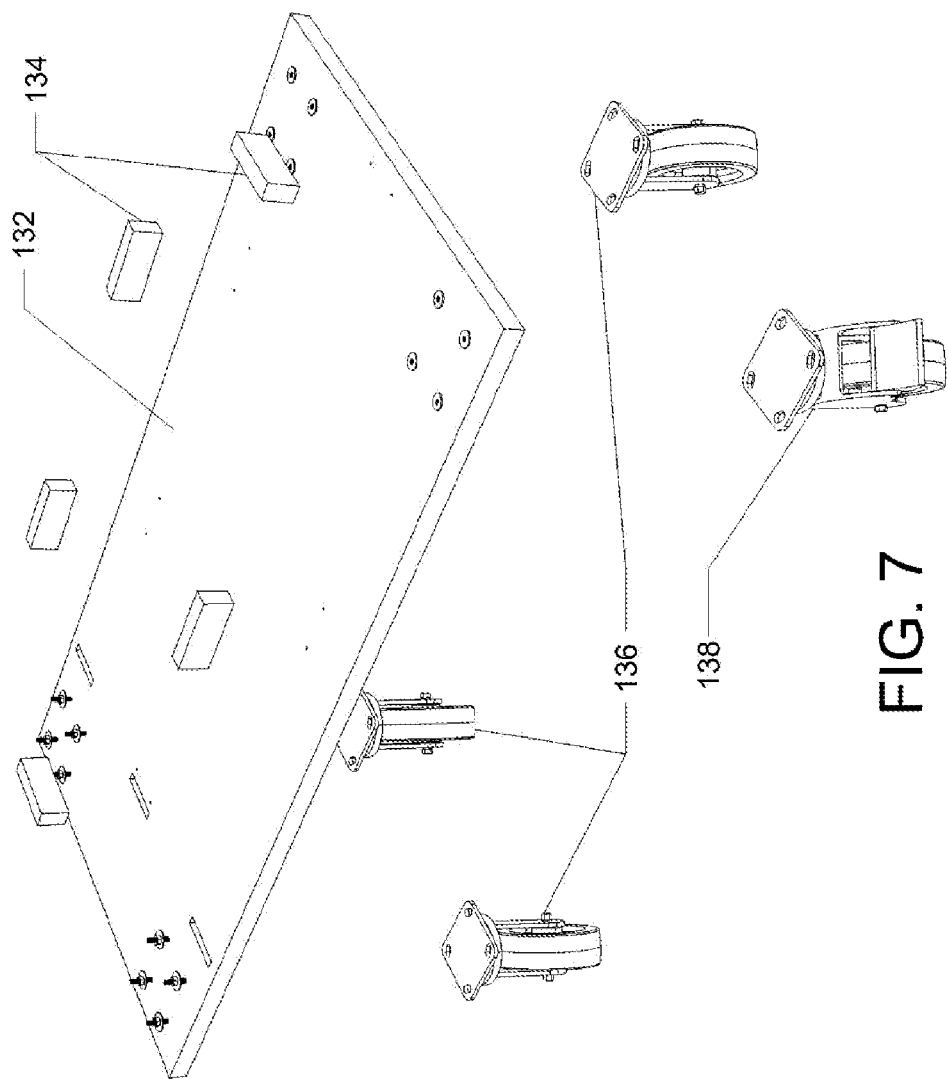
FIG. 7 is an exploded view of a platform.

FIG. 7 illustrates an exploded view of the platform 130. The platform 130 serves the dual function of furnishing a rigid bottom for the base unit and other assemblies, as well as allowing for the mobility of the unit 5. The platform 130 raises the top of the mattress 58 and coverlet 70 to counter height 30" to 36" (762 mm to 915 mm) above the ground. This permits attending of the patient by physicians, staff, and/or family from a standing position, but allows for visual monitoring of the patient while seated.

The reservoir 94 is supported by a deck 132 and held securely in place by chocks 134. The support structure 92 is mounted on the deck 132. The platform 130, deck 132 and chocks 134 are fabricated from wood. Alternately plastic, metal, honeycomb composite, or fiberglass reinforced plastic (FRP) composite may be used. An alternate embodiment of the platform may be to integrally engineer it into the bottom of the reservoir 94 and/or the support structure 92, instead of having it as a separate sub-assembly.

The unit 5 is moved on a floor or deck using four casters 136 that are attached to the platform 130, at least one of which is a locking caster 138. The locking caster 138 provides a means of securing the platform 130 in place on a floor or deck that is off-level. At least two of the casters 136 are to be free and thereby able to pivot to facilitate maneuvering in close or confined spaces. The combined load capacity of the casters is adequate to support the maximum filled weight of the unit 5 with a minimum safety factor of two. The wheels may be low-durometer polypropylene or equal to provide travel with a minimum of jarring. The undercarriage may be alternately embodied with two wheels secured to a fixed axle and two, wheels affixed to a steerable axle. At least one of the wheels is to be lockable.

Figure 8:
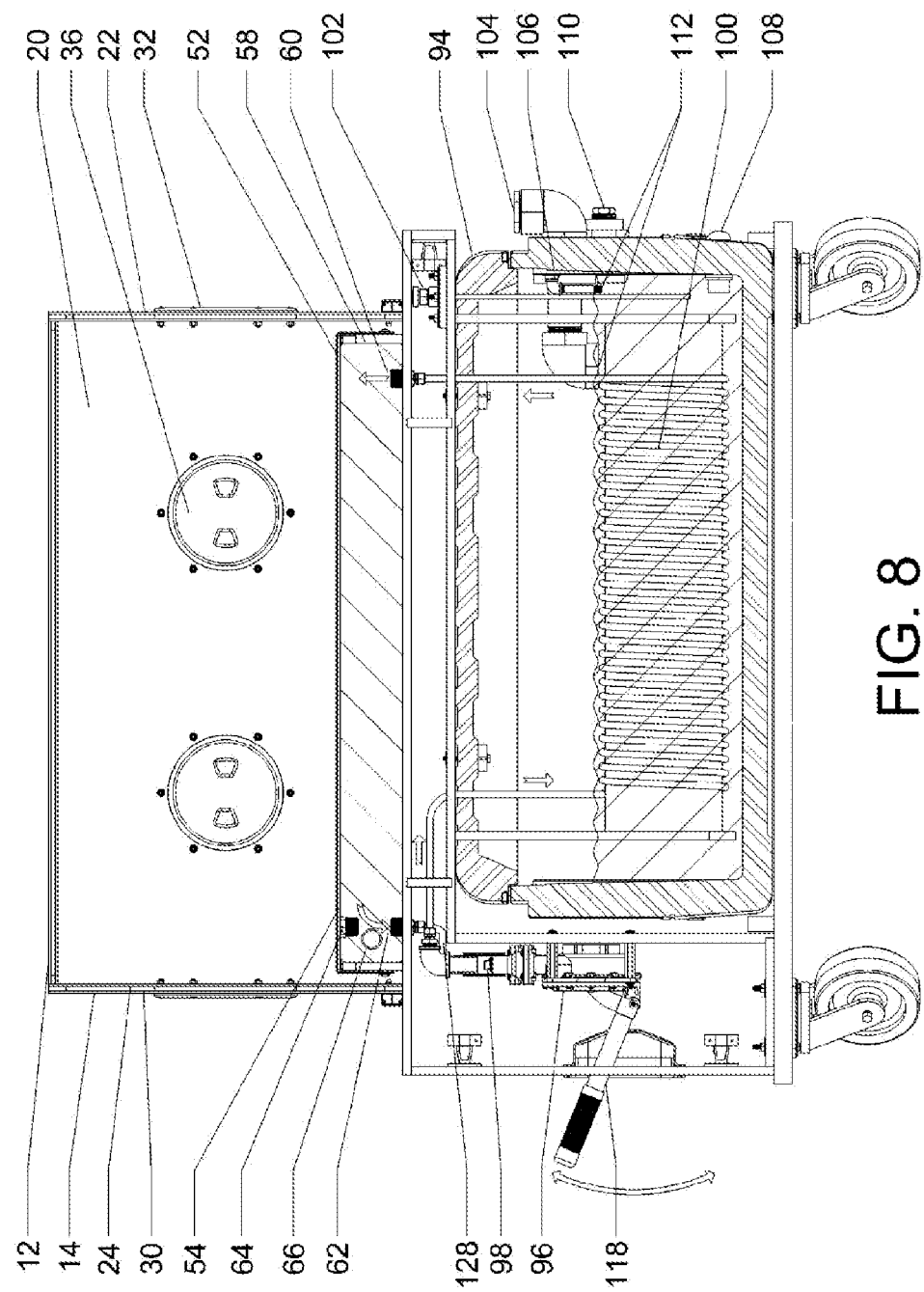
FIG. 8 is a cutaway view of the infant enclosure, mattress, coverlet, base unit and platform.

FIG. 8 illustrates a cutaway view of the infant enclosure 10, mattress 58, coverlet 50, base unit 80, and platform 130. When the pump 96 is actuated by the pump handle 118, water is pushed through a conduit 128 into the heat exchanger 100. The temperature of the water flowing through the heat exchanger 100 is changed, when a differential exists between the temperatures of the water inside the heat exchanger 100 and the water in the reservoir 94. The heated (or cooled) water from the heat exchanger 100 flows into the inlet port 60 of the mattress 58. At the opposite end of the mattress 58, water is removed at the outlet port 62 where it returns to the pump 96 through conduits 128 to repeat the cycle.

The temperature of the water inside the mattress 58 may be visually monitored by observing the mattress thermometer 66. When the desired temperature is reached, pumping of water through the heat exchanger 100 is stopped. To protect the patient from excessive heat, the flow of water through the heat exchanger 100 is automatically stopped by the thermal safety valve 98, which is preset to close at a non-hazardous temperature.

Water may be poured into or drained away from the mattress 58 and heat exchanger 100 through the fill-drain-vent port 64. The reservoir 94 is filled with enough water to cover the heat exchanger 100 through a reservoir fill 104. Air inside the reservoir 94 that is displaced by the water exhausts through a reservoir vent 106. The level of water inside the reservoir 94 may be visually monitored through the sight glass 110. The reservoir 94 is not overfilled because overfill protection 112 on the fill 104 and vent 106 directs excess water up these orifices. The temperature of water in the reservoir 94 may be monitored by observing the reservoir thermometer 102. Water may be drained from the reservoir 94 through the reservoir drain 108.

Water inside the mattress 58 heats (or cools) the top portion 52 of the coverlet 70. The patient is heated (or cooled) through intimate contact with the coverlet 70 and by exposure to conditioned air inside the infant enclosure 10. Since outside air may enter the infant enclosure 10 through the porthole-closures mesh 32, the coverlet 70 is fabricated with the insulation layer 54 to reduce the rate of change of temperature of water in the mattress 58 through convection.

The interior of the infant enclosure 10 is thermally and acoustically insulated from the ambient environment. Ambient air is thermally attenuated and ambient noise is acoustically reduced by the air gap between the inner panels 26 and the outer panels 30 that form the infant enclosure 10. Access to the interior of the infant enclosure 10 by insects and small foreign objects is restricted by the porthole closures-mesh 32 and porthole closures-solid 36.

Figure 9:
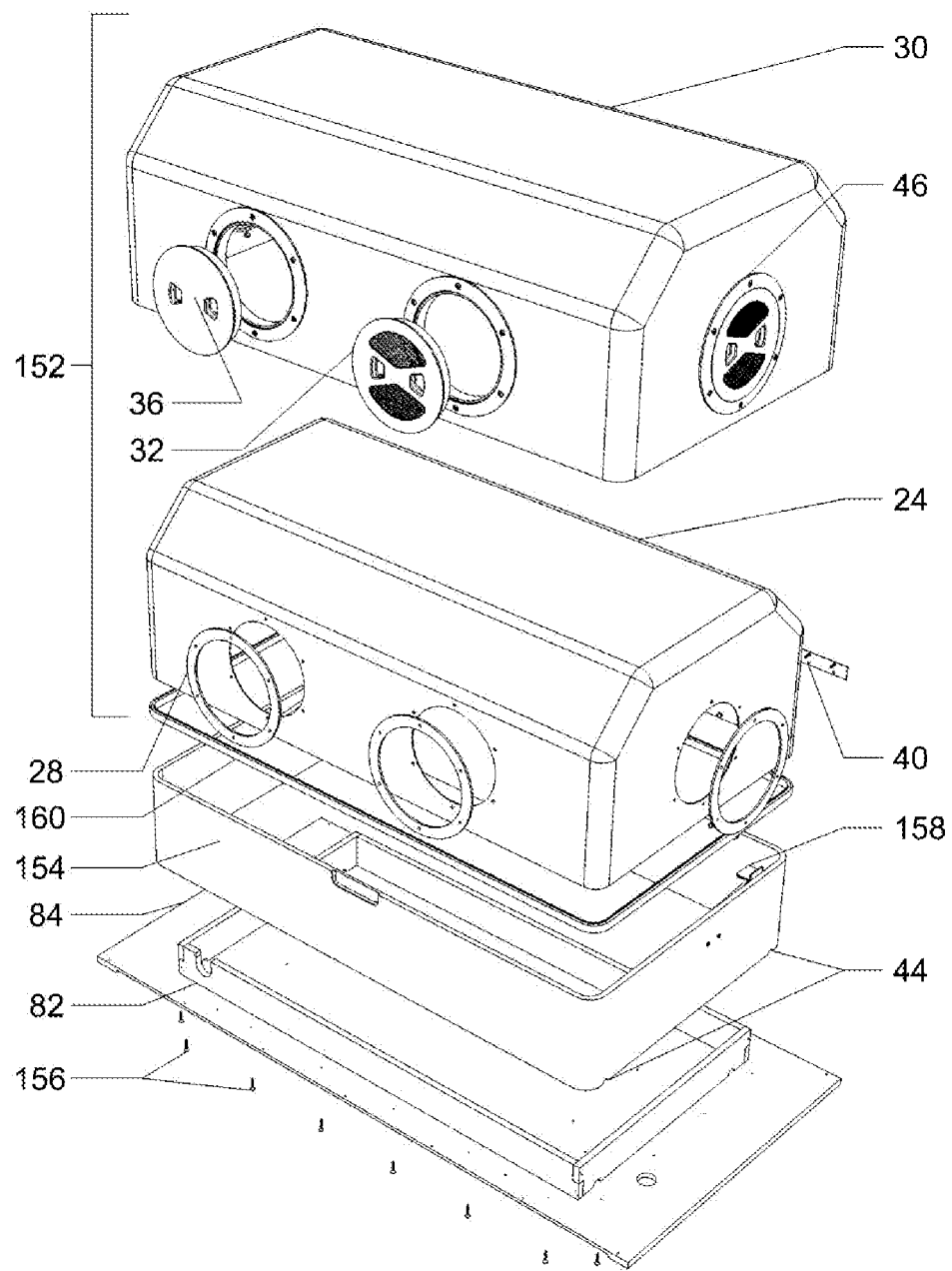
FIG. 9 is an exploded view of an alternate embodiment of the infant enclosure.
Figure 10:
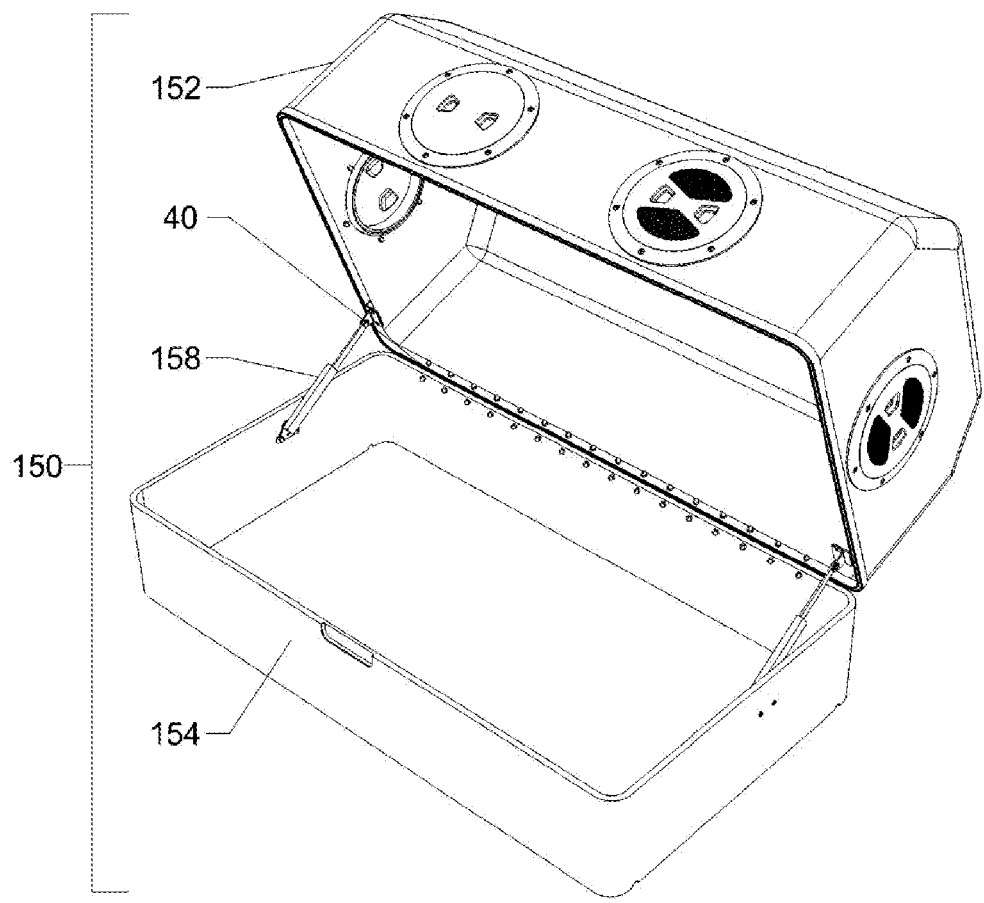
FIG. 10 is an isometric view of the alternative embodiment of the infant enclosure when in an open position.

Illustrated in FIG. 9 and FIG. 10, an alternate embodiment of the infant enclosure 10 is an infant enclosure 150 with no doors, which has a movable top 152 consisting of a box-like outer panel 30 and a box-like inner panel 24 that are connected at the bottom by a seal 160. The movable top 152 is connected to a fixed base 154 by a hinge 40. The movable top 152 and fixed base 154 define a chamber within for the patient. The enclosure 150 may be composed of rigid transparent material, for example, clear acrylic sheet (polymethyl methacrylate). Alternately, the enclosure 150 may be made of PETG (glycol modified polyethylene terphthalate), Lexan (polycarbonate), laminated (safety) glass, or tempered glass. The movable top 152 has laminated construction. The fixed base 154 may have laminated or solid construction.

The inner panel 24 and outer panel 30 of the enclosure 150 are held a uniform distance apart by porthole spacers 28, in addition to the seal 160. An air gap between the panels provides both a thermal and an acoustic barrier to reduce the rate of heat and sound conduction between the interior of the infant enclosure 150 and the ambient environment.

The movable top 152 may be fitted with one or more portholes 46 defining access passages there through. The porthole 46 may be securely held in place by fasteners and/or adhesive. Porthole closures-solid 36 that securely interlock with the porthole 46 are provided. Alternately, porthole closures-mesh 32 for ventilation and/or for providing a conduit for life-support tubes/cables for the patient are provided. Each porthole closure-mesh 32 securely interlocks with a porthole 46. Each enclosure 150 is fitted with one or more porthole closure-mesh 32 for the safety of the patient. Each porthole closure-mesh 32 is outfitted with a mesh 34 comprised of woven metal, plastic, and/or fabric to limit entry of insects and/or small airborne contaminants into the infant enclosure 150, while permitting flow of air. The passages furnish access to the inside the enclosure by physicians, health care workers, and/or the family of the patient without requiring that the enclosure be fully opened.

The movable top 152 is pivotally affixed to the fixed base 154 by a hinge 40. The hinge 40 is a piano hinge. Alternatively, butt hinges, glass hinges, or pivot hinges may be utilized.

The movable top 152 is held in an open position by one or more lid stays 158, which are affixed to the fixed base 154. When the movable top 152 is open, major access to the patient is permitted. The movable top 152 stays closed from its own weight. The fixed base 154 is attached to the top 84 of the base unit 80 with fasteners 156 and/or adhesive.

The infant enclosure 150 is outfitted with one or more drains 44. This safety feature provides a means to direct any inadvertent escape of liquids from inside the infant enclosure away from the baby. Multiple drains are preferred to insure proper flow, regardless of the orientation and level of the unit 5.

With respect to the above description then, it is to be realized that the optimum dimensional relationships for the parts of the invention, to include variations in size, materials, shape, form, function, and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A neonatal intensive care unit apparatus, comprising in combination:
   a support structure having a top platform and a bottom platform;
   conduits for fluid flow;
   a pump connected to the conduits and affixed to the support structure;
   a reservoir containing fluid;
   a heat exchanger support mounted to the bottom panel of the support structure;
   a heat exchanger positioned on the heat exchanger support, and the heat exchanger being operatively connected to the pump;
   a mattress mounted on the top platform of the support structure, whereby the mattress is in fluid connection with the heat exchanger; and
   a transparent enclosure having a top wall, side walls, a back wall and front doors defining a chamber therein, mounted on the support structure and enclosing the mattress, and further whereby the side walls and the back wall each are comprised of an inner panel and an outer panel, the panels having a uniform distance therebetween.

2. The apparatus of claim 1, further comprising a horizontal platform with wheels mounted at opposite corners, and whereby the support structure is integrated with the platform.

3. The apparatus of claim 1, whereby the fluid is water.

4. The apparatus of claim 1, further comprising a pump handle operatively engaged to manually activate the pump.

5. The apparatus of claim 1, further comprising a mattress retainer affixed to the top platform of the support structure, whereby the retainer is of predetermined size to secure the mattress.

6. The apparatus of claim 5, further comprising a coverlet having a top layer, an insulation layer and a bottom layer, whereby the coverlet is mounted over an outer surface of the mattress.

7. The apparatus of claim 6, whereby the coverlet is secured to the mattress retainer by catches.

8. The apparatus of claim 1, whereby the front doors are pivotally affixed to the side walls by hinge means.

9. The apparatus of claim 1, further comprising at least one panel spacer having a top edge, a bottom edge substantially opposed the top edge, and a pair of parallel side edges between the top edge and the bottom edge, mounted between the inner panels and the outer panels of the enclosure.

10. A transparent enclosure for use in a neonatal intensive care unit apparatus, comprising in combination:
    a covering comprising an inner panel having a top portion, side portions, a back portion, and a front portion, and an outer panel having a top portion, side portions, a back portion, and a front portion, whereby the inner panel and the outer panel are spaced at a uniform distance;
    a seal connecting the inner panel of the top covering and the outer panel of the top covering at bottom peripheral edges; and
    at least one panel spacer having a top edge, a bottom edge substantially opposed the top edge, and a pair of parallel side edges between the top edge and the bottom edge, mounted between the inner panel and the outer panel of the top covering.

11. The enclosure of claim 10, further comprising a base pivotally affixed by hinge means to the covering, whereby the covering and the base define a chamber therein.

12. The enclosure of claim 11, further comprising at least one porthole defining access passage therethrough formed and mounted through the inner panel of the top covering, the panel spacers, and the outer panel of the covering.

13. The enclosure of claim 12, further comprising solid porthole closures detachably coupled to the portholes.

14. The enclosure of claim 12, further comprising porthole closures having mesh material detachably coupled to the portholes.

15. A neonatal intensive care unit apparatus, comprising in combination:
- a support structure having a top platform and a bottom platform;
- conduits for fluid flow;
- a pump connected to the conduits and affixed to the support structure;
- a reservoir containing fluid;
- a heat exchanger support mounted to th bottom panel of the support structure;
- a heat exchanger positioned on the heat exchanger support, and the heat exchanger being operatively connected to the pump;
- a mattress retainer affixed to the top platform of the support structure;
- a mattress mounted on the mattress retainer, whereby the mattress is in fluid connection with the heat exchanger;
- a transparent enclosure having a top wall, side walls, a back wall front doors defining a chamber therein, mounted on the support structure and enclosing the mattress, and further whereby the side walls and the back wall each are comprised of an inner panel and an outer panel, the panels having a uniform distance therebetween; and
- at least on panel spacer having a top edge, a bottom edge substantially opposed the top edge, and a pair of parallel side edges between the top edge and the bottom edge, mounted between the inner panel and the outer panel of the enclosure.

16. The apparatus of claim 15, further comprising at least one porthole defining access passage therethrough formed and mounted through the inner panel of the top covering, the panel spacers, and the outer panel of the enclosure.

17. The apparatus claim 15, further comprising a first the further thermometer disposed on the reservoir and a second thermometer disposed on the mattress.

* * * * *